United States Patent [19]

Kruse et al.

[11] Patent Number: 5,448,997
[45] Date of Patent: Sep. 12, 1995

[54] HEART PACING PULSE DETECTION SYSTEM

[75] Inventors: John M. Kruse, Columbia Heights; Cameron J. Kaszas, Brooklyn Park; C. Gary Nelson, Maple Grove, all of Minn.

[73] Assignee: Medtronic, Inc., Minneapolis, Minn.

[21] Appl. No.: 138,157

[22] Filed: Oct. 15, 1993

[51] Int. Cl.6 ............................... A11P 5/04
[52] U.S. Cl. ...................... 128/697; 607/27
[58] Field of Search ............ 128/696, 697, 699; 607/27; 364/413.01–413.03, 413.05, 413.06, 413.13

[56] References Cited

U.S. PATENT DOCUMENTS

| | | | |
|---|---|---|---|
| 4,574,813 | 3/1986 | Regan | 128/697 |
| 4,664,116 | 5/1987 | Shaya et al. | 128/419 PT |
| 4,934,376 | 6/1990 | Armington | 128/696 |
| 4,974,597 | 12/1990 | Walloch | 128/700 |
| 5,010,888 | 4/1991 | Jadvar et al. | 128/696 |
| 5,012,411 | 4/1991 | Policastro et al. | 364/413.06 |
| 5,022,404 | 6/1991 | Hafner | 128/696 |
| 5,029,082 | 7/1991 | Shen et al. | 364/413.06 |
| 5,127,401 | 7/1992 | Grevious et al. | 128/419 PT |

*Primary Examiner*—William E. Kamm
*Assistant Examiner*—Marianne Parker
*Attorney, Agent, or Firm*—Reed A. Duthler; Harold R. Patton

[57] ABSTRACT

A system including a process for enhancing detection of a pacing artifact in a patient having artificially paced myocardial contractions. The detection is accomplished by sensing seven EKG leads. Each lead provides a view of the heart from a different angle. The process relies on differentially amplifying the sensed pulses separately and passing the pulses through a filter. An algorithm is utilized to detect the noise level and the pacing artifact amplitude, and automatically select a proper trigger level. False pacing artifacts are eliminated by use of the software qualification. The principal is that if the hardware differentiator produces a signal due to noise or a pacing artifact, an interrupt is generated.

14 Claims, 10 Drawing Sheets

ENLARGED PACING ARTIFACT

HEART PACING PULSE DETECTION SYSTEM

BACKGROUND OF THE INVENTION

1. Field of the Invention

The present invention relates to the pacing of a heart, and more particularly, pertains to detection of a pacing artifact in an ECG signal.

2. Description of the Prior Art

Previous prior art patents rely solely on analog circuitry to filter out all but the high frequency edges of pacing pulses. There are many variations on the types of filters such as differentiator, or high pass filter, band pass filter, or combinations thereof; filter parameters such as cutoff frequencies, gains, etc.; and, the circuit implementations used for the filters.

U.S. Pat. No. 5,010,888 issued to Jadvar et al. describes variations on analog circuitry to detect and remove pacemaker pulses from an ECG signal (as opposed to highlighting them). Removal is desirable when the pacing pulses are large, and cause the ECG to be difficult to interpret, either from an ECG recorder or by a computerized ECG analysis system. U.S. Pat. No. 4,664,116 issued to Shaya et al. describes an analog circuit to detect pacemaker pulses, utilizing an adjustable detection threshold. U.S. Pat. No. 5,022,404 issued to Hafner describes analog circuitry to detect pacemaker pulses from an ECG signal(s), with the additional purpose of storing and/or transmitting the signal(s) to another location. U.S. Pat. No. 5,127,401 issued to Grevious describes analog circuitry to detect pacemaker pulses, utilizing multiple simultaneous lead vectors to improve the signal to noise ratio. U.S. Pat. No. 5,029,082 issued to Shen et al. describes a system that utilizes digital signal processing techniques and integrated circuits to do a variety of processing on various bioelectric signals such as ECG, VGG, EEG, etc.

Previous prior art devices are plagued by the following problems; noise from patient movements, bad lead connections, interference from pacemaker telemetry systems or other electrical equipment nearby. The problems could be erroneously detected as pacing pulses. In designing to eliminate the noise problem sufficiently, the sensitivity of previous inventions has been compromised. This becomes more of a problem as the trend toward using lower pacing energies whenever possible continues. Previous inventions can not automatically adapt to a wide variety of signal conditions. In addition, pacemakers utilizing minute ventilation (MV) sensors, which deliver a series of current pulses at a high frequency, pose a problem to previous inventions. These current pulses, used to measure the impedance of the heart, are erroneously detected as pacing pulses.

The present invention overcomes the disadvantages of the prior art by providing a heart pacing pulse detection system such as for a pacemaker programmer.

SUMMARY OF THE INVENTION

The general purpose of the present invention is a system including a process for enhancing detection of the pacing artifact in a patient having artificially paced myocardial contractions. The detection is accomplished by sensing seven EKG leads. Each lead provides a view of the heart from a different angle. The multiple views of the heart is quite important due to the recent advances in artificially pacing the heart. The recent advances now allow the heart to be artificially paced with very small and narrow amplitude pulses. The pulses are now small enough where they are not detectable from the skin surface unless the vector of detection is correct.

This process relies on differentially amplifying the pulses separately and passing the pulses through a low pass filter. The signals are not summed because several of the 7 leads may not have any signal present at all. The effect of summing the 7 signals would be to just add noise to the good signals.

The pulses that are encountered can vary over 10,000 times in amplitude and several hundred times in width. One detection level is no longer adequate for all of the possible pulse amplitudes and widths that could be encountered. The process uses a closed loop technique to automatically determine the correct detection level.

Reliable detection of the pacing artifact is extremely important in monitoring and programming implantable pacemakers. It is necessary to accurately determine whether and when a pacing pulse has occurred and the width of the pacing pulse.

The pacing artifact circuit is programmable. The circuit has eight levels of detection that can be selected from the processor. An algorithm is utilized to detect the noise level and the pacing artifact amplitude, and automatically select the right trigger level.

The system eliminates false pacing artifacts by utilizing the software qualification. The principal is that if the hardware differentiator produces a signal due to noise or a pacing artifact, an interrupt is generated.

Significant aspects and features of the present invention include the use of a digital signal processor system which couples decision making/control capabilities to an analog detection circuit; the ability to utilize past information (the detect rate, detect pattern, and width of the previous pacing pulses) to discriminate pacing pulses from noise; the ability to utilize information from the pacemaker and/or programmer to aid in the discrimination of pacing pulses from noise; the ability to adjust the detection threshold (sensitivity) to one of 8 different levels, optimally selected based on the signal to noise ratio; the ability to automatically adjust the input EGG lead to the one with the highest signal to noise ratio; the use of recursive digital filters to keep running counts of the number detections registered by the analog detection circuitry within various time windows; and, software algorithms which synthesize the information and perform the control.

Other significant aspects and features of the present invention include coupling analog detection circuitry to a digital signal processor (DSP). The DSP provides additional intelligence to, and control of, the analog detection circuitry.

Having described embodiments of the present invention, it is a principal object hereof to provide a heart pacing pulse detection system.

One object of the present invention is to provide sophisticated pulse detection criteria, data acquisition, and automatic adjustment capabilities.

Another object of the present invention is to also provide a more accurate determination of the presence of pacing pulses than previous systems—and allows detection of lower energy pacemaker pulses under noisier signal conditions.

A further object of the present invention is to discriminate between MV sensor stimuli and pacing pulses.

BRIEF DESCRIPTION OF THE DRAWINGS

Other objects of the present invention and many of the attendant advantages of the present invention will be readily appreciated as the same becomes better understood by reference to the following detailed description when considered in connection wit the accompanying drawings, in which like reference numerals designate like parts throughout the figures thereof and wherein.

DETAILED DESCRIPTION OF THE PREFERRED EMBODIMENTS

Figure 1:
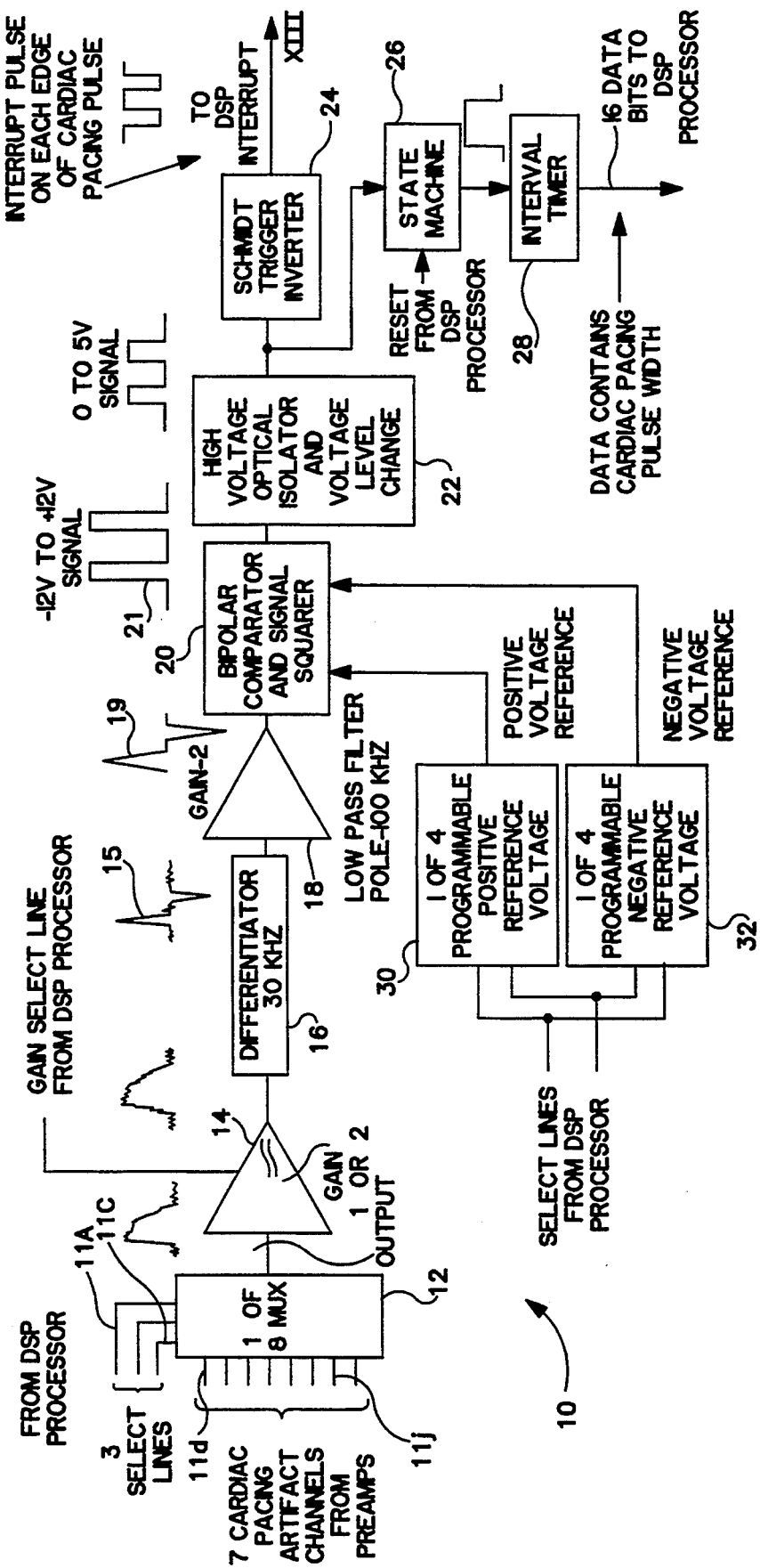
FIG. 1 illustrates a block diagram of a heart pacing pulse detection block diagram.
Figure 3A:
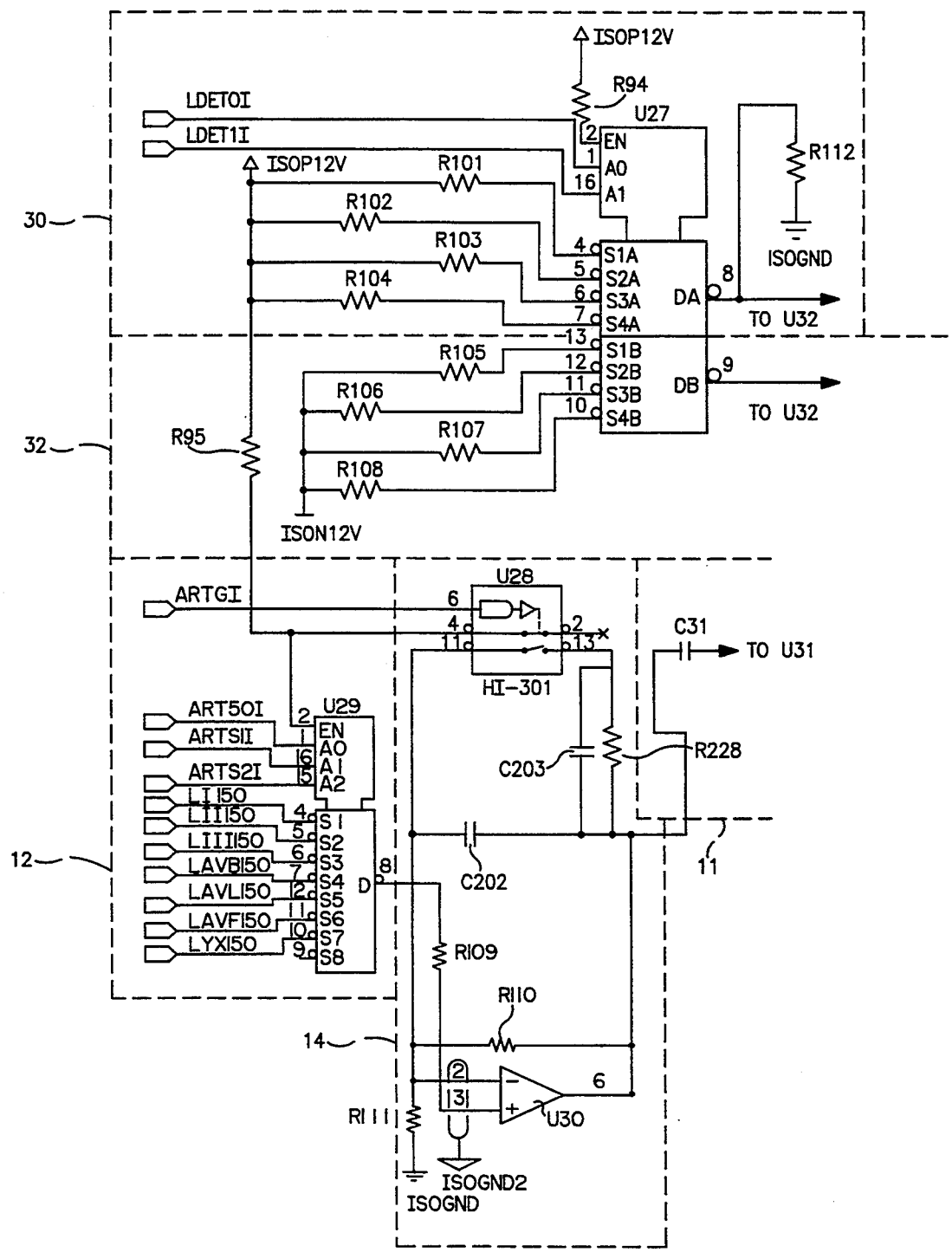
FIGS. 3A and 3B illustrates an electrical circuit schematic diagram of the heart pacing pulse detection system.
Figure 3B:
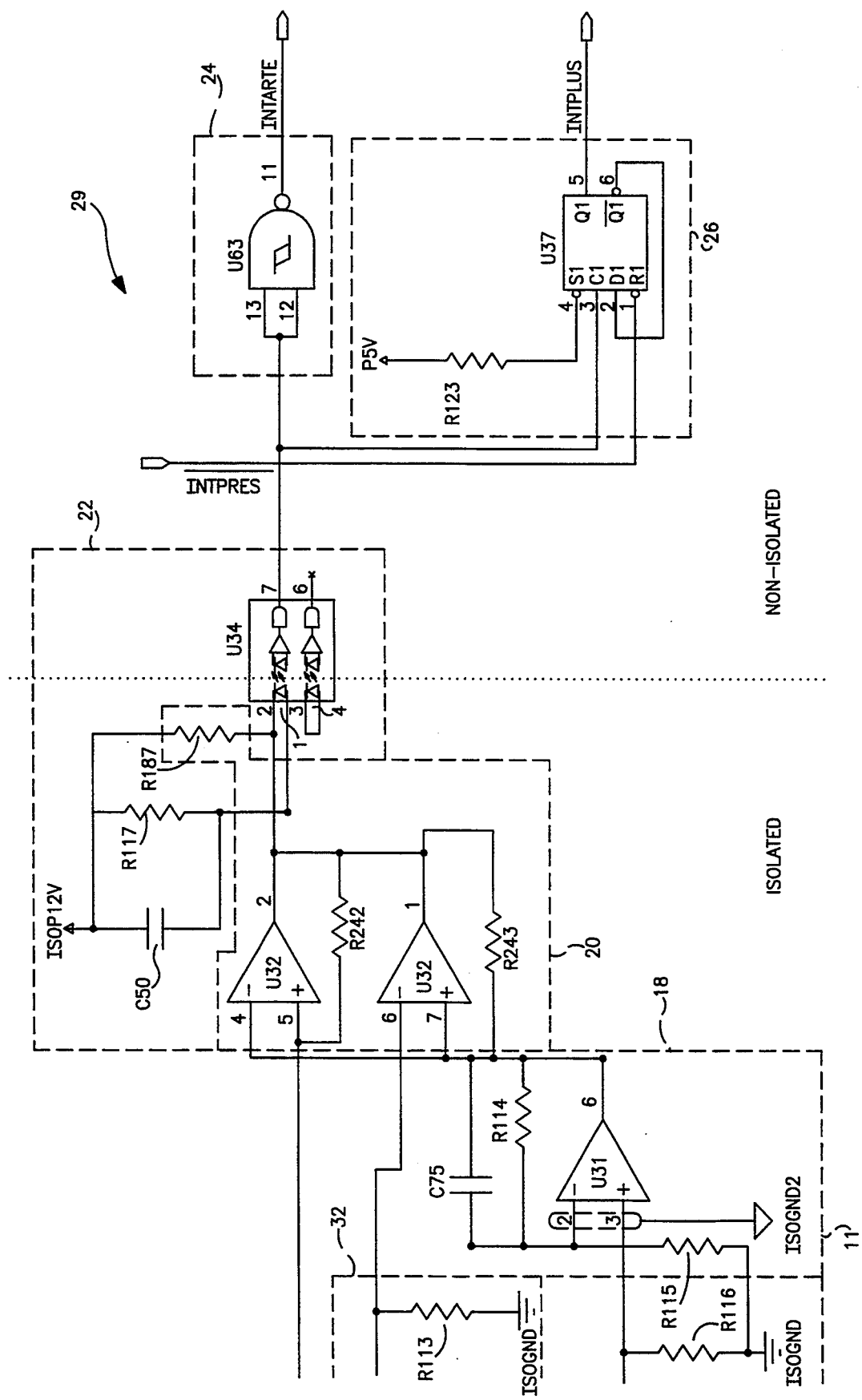

FIG. 1 is a block diagram of a heart pacing pulse detection system 10. There are 7 pacing artifact signals that connect into a 1 of 8 Multiplexer 12. There are 3 select lines 11a–11c that come from a DSP processor that controls which one of the 7 input channels 11d–11j for pacing signals are outputted out of the 1 of 8 multiplexer 12 as also illustrated in FIGS. 3A and 3B. U29 on the electrical circuit schematic diagram of FIGS. 3A and 3B is the 1 of 8 multiplexer.

The signal then is amplified by a gain of 1 or 2 by an operational amplifier 14. The gain setting is controlled from the DSP processor, and is set to the appropriate gain depending on the amplitude of the pacing artifact. This gain stage has a low pass pole which eliminates some of the high frequency noise that is contained in the signal. This gain stage consists of R109, R110, R111, R228, C202, C203, U28, and U30 of FIGS. 3A and 3B.

The signal is then sent into a differentiator 16 (a high pass filter) which has the pole set at 30 KHZ. This frequency was found to be optimal for Medtronic pacemakers. The frequency is high enough to effectively filter out all naturally occurring biopotential signals but not filter out even the slowest pacing artifacts. The resulting signal 15 is illustrated on the block diagram of FIG. 1. The differentiator consists of C31 and R116 of FIGS. 3A and 3B.

The signal is then passed through a low pass filter 18 with the pole set to 100 kHZ. This stage is also a gain stage with a gain of 2. This stage eliminates some of the high frequency noise present in the signal as illustrated in the resultant signal 19. This low pass filter 18 consists of R114, R115, C75 and U31 of FIGS. 3A and 3B.

The signal is now passed into a bipolar comparator and signal squarer 20. The signal is compared to a positive reference voltage and a negative reference voltage. The portion of the signal that has magnitudes greater than the two reference signals produce a square pulse. The bipolar signal squarer 20 consists of U32a and U32b, R242, R243, R181, C152 and C153 of FIG. 3A and 3B.

The positive voltage reference 30 that the bipolar comparator 20 uses is programmable from the DSP processor. There are four reference voltages available to select from. Thus from the DSP processor it is possible to vary the gain of the incoming pacing artifact signal and select one of any four reference voltages. This effectively provides 8 positive reference voltages. This is extremely important since pacing artifacts can vary in amplitude by a factor of 10000. The positive voltage reference block consists of one half of U27, and all of R101, R102, R103, R104, and R112 of FIGS. 3A and 3B.

The negative voltage reference 32 that the bipolar comparator uses is programmable from the DSP processor. There are four reference voltages available to select from. Thus from the DSP processor it is possible to vary the gain of the incoming pacing artifact signal and select one of any four reference voltages. This effectively gives us 8 negative reference voltages. This is extremely important since pacing artifacts can vary in amplitude by a factor of 10000. The negative voltage reference block consists of one half of U27, and all of R105, R106, R107, R108, and R113 of FIGS. 3A and 3B.

The squared up signal 21 is now passed into an optical isolator 22 which is needed to isolate the patient from the rest of the circuitry. The optical isolator 22 is capable of withstanding high voltage potentials across the isolation barrier. The output of the optical isolator block 22 is a 5 volt TTL compatible signal. The optical isolator block 20 consists of U34, R117, and C50.

The signal is now run into a Schmidtt trigger inverter 24 which provides hysteresis. The edges produced by the optical isolator 22 are too slow to be run directly into the DSP interrupt input. The Schmidtt trigger block 24 inverts the signal to the correct polarity and speeds up the edges to the required specifications of the DSP processor. The Schmidtt trigger block 20 consists of one fourth of U63.

The signal leaving the optical isolator 22 is also run into a small state machine 26. This state machine 26 simply takes the pulses and creates one pulse that is the width of the original pacing artifact. The state machine 26 can be reset by the DSP processor via an output. The state machine consists of one half of U37, and R123 of FIGS. 3A and 3B.

The output of the state machine 26 is fed into a programmable interval timer 28 that is used to measure the pulse width. The output from the interval timer 28 is 2 bytes of 8 bits each in width which contains the number of clock periods wide that the pacing artifact was. The interval timer block 28 consists of U55.

Figure 2:
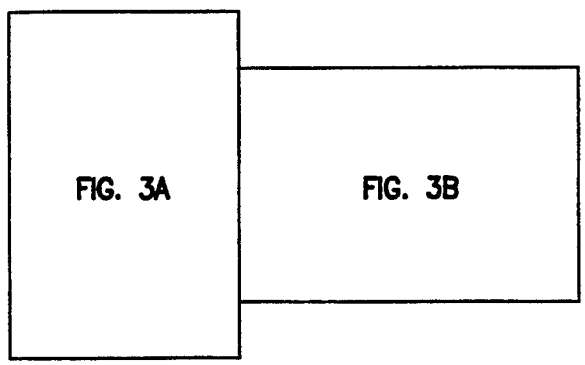
FIG. 2 illustrates the orientation and alignment of FIGS. 3A and 3B.

FIG. 2 illustrates the orientation and alignment of FIGS. 3A and 3B.

FIGS. 3A and 3B illustrates the electrical circuit schematic diagram 29 of the heart pacing pulse detection system 10.

Corresponding to blocks 30 and 32 is a 1 of 4 programmable positive reference voltage. U27 is a dual 4 channel analog multiplexer. One half of U27 is used to provide a selection of 1 of 4 resistors R101-R104 to work as a voltage reference for U32 via an instruction from the DSP processor. R101 is a positive voltage reference resistor and works in conjunction with R112 to provide a positive voltage reference for the comparator 20. R102 is a positive voltage reference resistor and works in conjunction with R112 to provide a positive voltage reference for the comparator 20. R103 is a positive voltage reference resistor and works in conjunction with R112 to provide a positive voltage reference for the comparator 20. R104 is a positive voltage reference resistor and works in conjunction with R112 to provide a positive voltage reference for the comparator 20. R112 is a positive voltage reference resistor and works in conjunction with R101, or R102, or R103, or R104 to provide a positive voltage reference. The other half of the dual 4 channel analog multiplexer U27 is also used to provide a selection of 1 of 4 resistors R105-R108 to work as a voltage reference via an instruction from the DSP. R105 is a negative voltage reference resistor and works in conjunction with R113 to provide a negative voltage reference for the comparator 20. R106 is a negative voltage reference resistor and works in conjunction with R113 to provide a negative voltage reference for the comparator 20. R107 is a negative voltage reference resistor and works in conjunction with R113 to provide a negative voltage reference for the comparator 20. R108 is a negative voltage reference resistor and works in conjunction with R113 to provide a negative voltage reference for the comparator 20.

Corresponding to block 12, U29 is a 8 channel analog multiplexer U29 which provides for selection of any 1 of 7 cardiac input channels 11d-11j for pacing signals from preamps via an instruction from the DSP processor. Corresponding to block 14, U30 is a ultra low noise precision OP amp which amplifies the selected cardiac pacing signal. R110 is a feedback resistor for gain=2 which is a feedback resistor for U30 for a gain of 2. R111 is a gain resistor which sets the gain for U30 in conjunction with R110 or R228. R228 is a feedback resistor for gain=1 which is a feedback resistor for U30 for a gain of 1. R109 is an input bias current balancing resistor which reduces offset voltage of U30 by balancing input impedance. C202 is a low pass pole capacitor, gain=2, which is a capacitor that works in conjunction with R110 to create a low pass pole to eliminate high frequency noise for a gain=2. U28 is an analog switch which switches feedback resistors and capacitors for U30 via an instruction from the DSP processor. By switching the feedback the gain is switch from 1 to 2 or 2 to 1. C203 is a low pass pole capacitor, gain=1, which is a capacitor that works in conjunction with R228 to create a low pass pole to eliminate high frequency noise for a gain=1.

Corresponding to block 16, C31 is a differentiator capacitor which works in conjunction with R116 to create a high pass pole filter. R116 is a differentiator resistor which works in conjunction with C31 to create a high pass pole filter.

Corresponding to block 18, R115 is a gain resistor which works in conjunction with R114 to create a gain of 2 for U31. R114 is a feedback resistor for U31 for a gain of 2. C75 is a low pass pole capacitor which works in conjunction with R114 to create a low pass filter to eliminate high frequency noise. U31 is an ultra low noise precision op amp which amplifies the differentiated signal and filters out high frequency noise.

Corresponding to block 20, U32a and U32b are voltage comparators which include the differentiated signal to reference voltage and produces a square pulse if the differentiated signal is greater than the reference signal. R242 and R243 are hysterysis resistors which provides hysterysis for the comparator to avoid oscillations. R187 is a open collector pull-up which provides current for the open collector output of U32a and U32b.

Corresponding to block 22, U34 is a high voltage withstanding optical isolator which provides high voltage protection and patient isolation via an optical link. The input is ±12v and the output is +5v which is TTL compatible. R117 is a current supply for optical isolator 22 which provides current drive for the light emitting diode in the optical isolator 22. C50 is a speed up capacitor for the optical isolator used to speed up the switching speed of the optical isolator 22 by providing a high frequency bypass of R117.

Corresponding to block 24, U63 is a Schmidtt trigger TTL "AND" gate which speeds up the slow edges of the optical isolator 22 and inverts the signal to be run into the DSP interrupt.

Corresponding to state machine block 26, U37 is a D type flip flop which takes the two pulses (one for the leading edge and one for the trailing edge of the pacing artifact) and creates one pulse.

Corresponding to block 28 of FIG. 1, an interval timer is used to clock the width of the pulse from the state machine. This width corresponds to the width of the original cardiac pacing pulse.

Figure 4A:
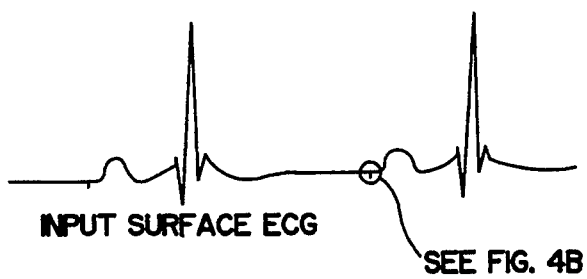
FIG. 4A illustrates an input surface ECG and FIG. 4B illustrates an enlarged pacing artifact.
Figure 4B:
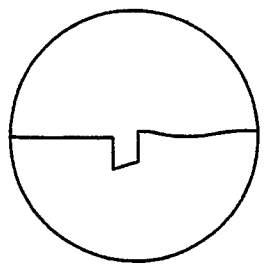

FIG. 4A illustrates an input surface ECG and FIG. 4B illustrates an enlarged pacing artifact.

MODE OF OPERATION

Figure 5:
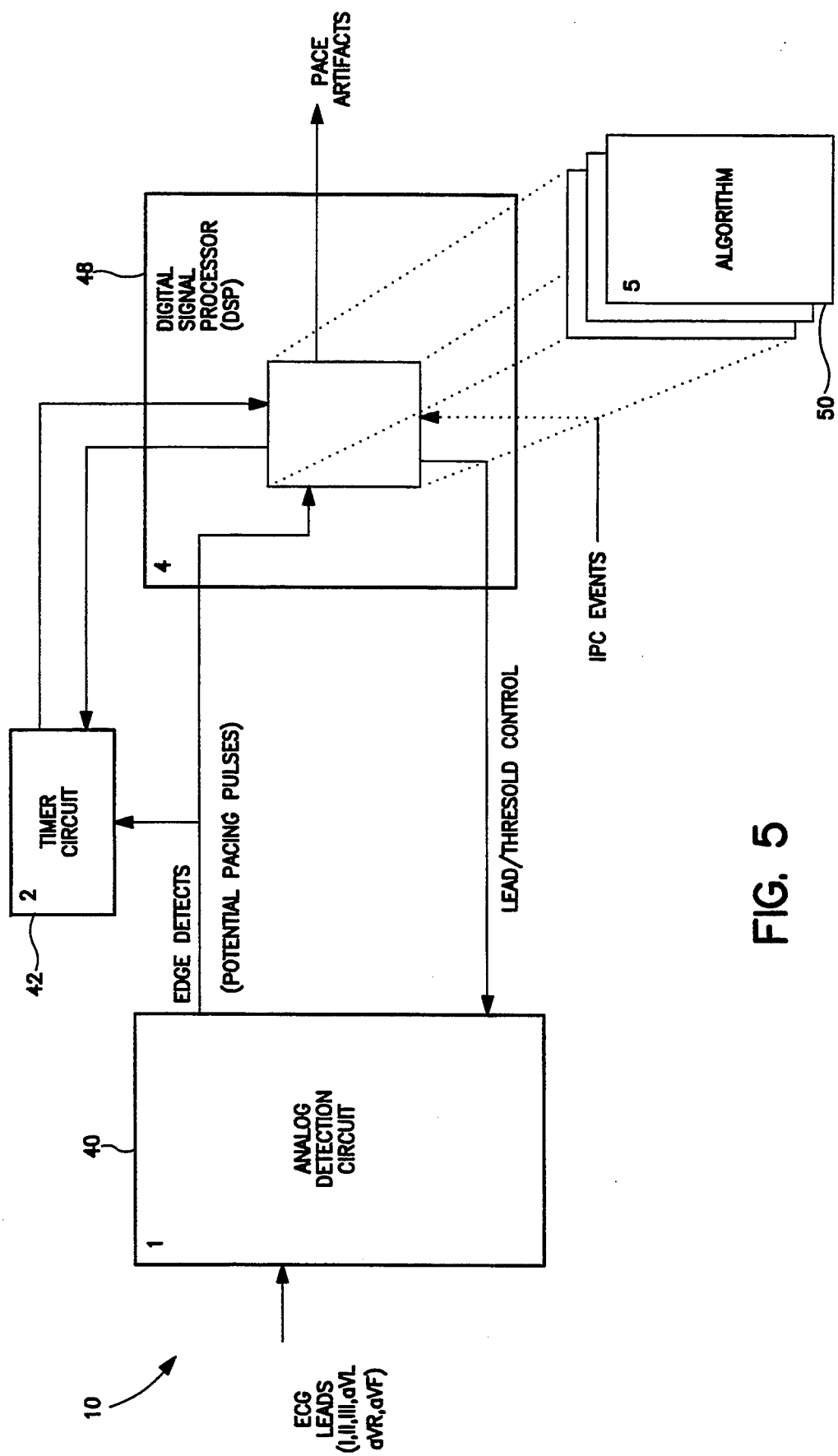
FIG. 5 illustrates a block diagram of a pacing pulse detection system.

FIG. 5 illustrates a block diagram of the pacing pulse detection system 10 including the detection circuit 30, the timer 42, the digital signal processor (DSP) 48, and the algorithm 50 which executes on the DSP. The algorithm 50 distinguishes the system and controls the operation of the blocks, based on an analysis of their outputs.

The algorithm is able to:
(1) optimally adjust the detection threshold (to be more sensitive if needed, or less sensitive if not needed);
(2) discriminate pulses from noise based on pulse width, interval between pulses, time history of detections, time patterns of detections, correlation with marker and/or EGM data (if available), and knowledge of programmer interaction with pacemaker by an uplink/downlink.

Figure 6:
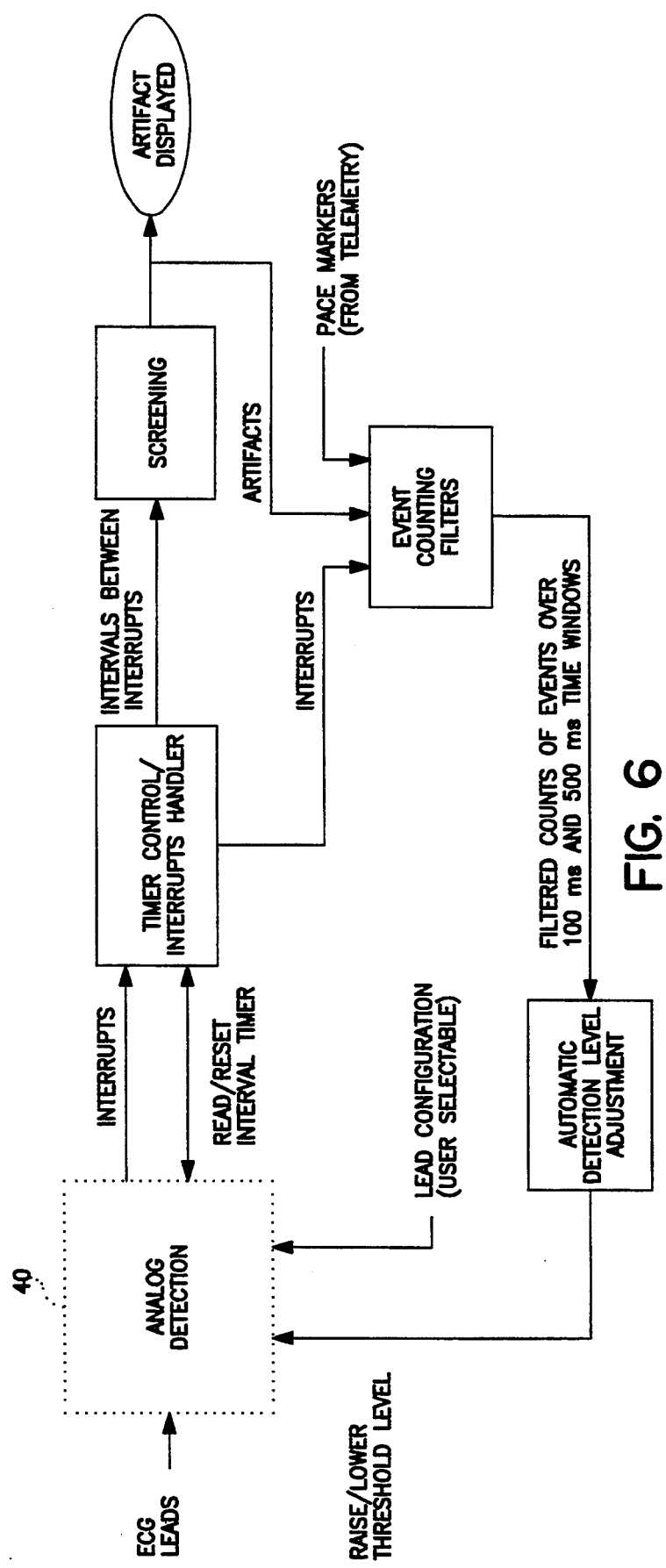
FIG. 6 illustrates an overview block diagram of the pacing pulse detection system.

FIG. 6 is an overview block diagram of the pacing pulse detection systems algorithm 50. This is further described in detail in FIGS. 7-10.

Figure 7:
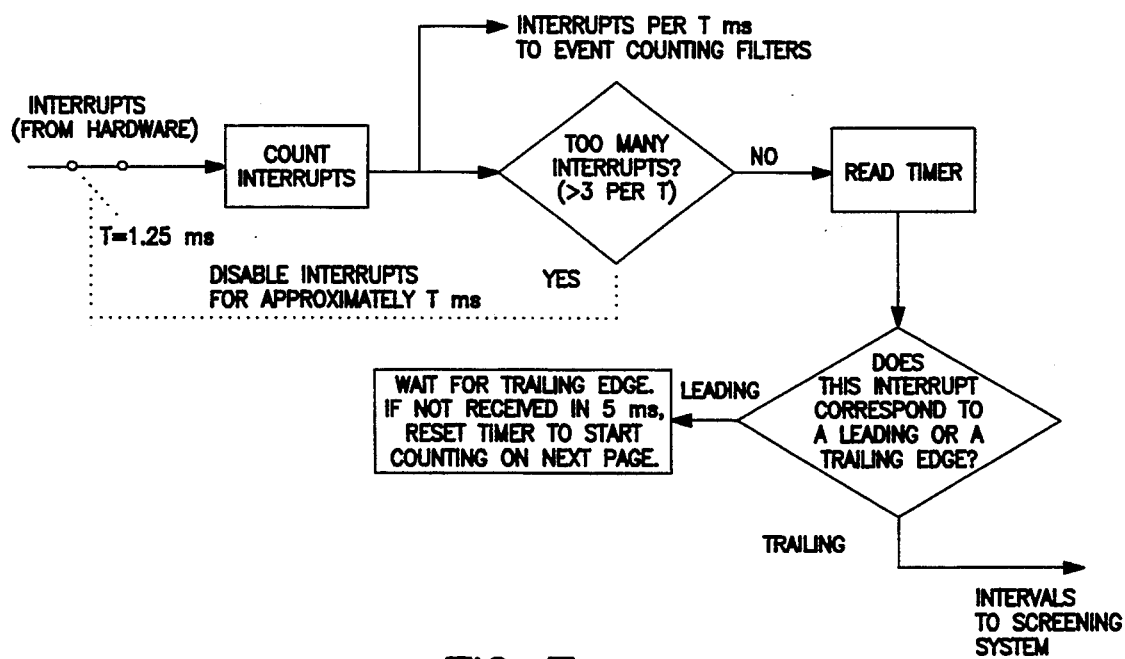
FIG. 7 illustrates a timer control/interrupt handler flow chart.

FIG. 7 is the Timer Control/Interrupt Handler algorithm which is responsible for sorting the information from the hardware detection circuit. The hardware detects leading and trailing edges of pacing pulses, and interrupts the DSP. Each interrupt triggers the DSP to execute the timer control/interrupt handler sequence of FIG. 7. The interrupts are counted during 1.25 ms time intervals. Every 1.25 ms. the count is passed to the event counting filters, and the count restarted. If the count ever exceeds 3 in a 1.25 ms interval, the interrupt line to the DSP is disabled, and no interrupts are processed for the remainder of the 1.25 ms interval. This insures that the processor does not spend an inordinate amount of time servicing interrupts in the event of excessive noise on the signal. This block also reads the interval timer hardware, which is being started and stopped on alternating interrupts by the hardware. The DSP has to determine which interrupts correspond to trailing edges, or stopping of the timer. This is done by reading the timer twice, and determining if the count has changed from the first reading to the second reading. If the count has changed, then the timer is in the process of counting, and the interrupt was due to a leading edge. No further processing is performed until the trailing edge comes. When the next interrupt comes in, the count is read from the timer, and passed to the screening algorithm. If the trailing edge does not come before 5 ms expires (timed by the software), the hardware timer is reset and armed to treat the next edge as a leading edge.

Figure 8:
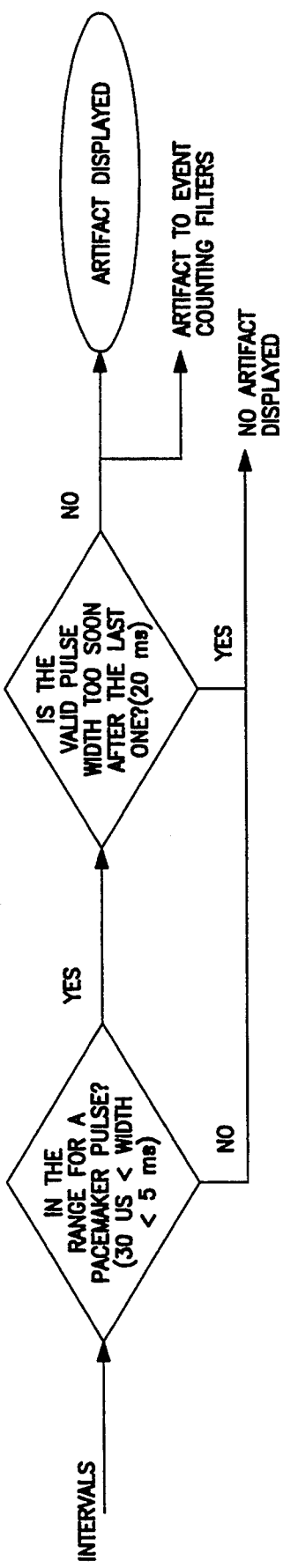
FIG. 8 illustrates a flow chart for a screening flow chart.

FIG. 8 is the screening algorithm which insures that only pulses in the range of known values for pacemaker pulses are marked as artifacts, and also that artifacts can come no closer together than 20 ms. Twenty (20) ms is the lower limit for pacing intervals with current pacemakers and pacemaker therapies.

Figure 9A:
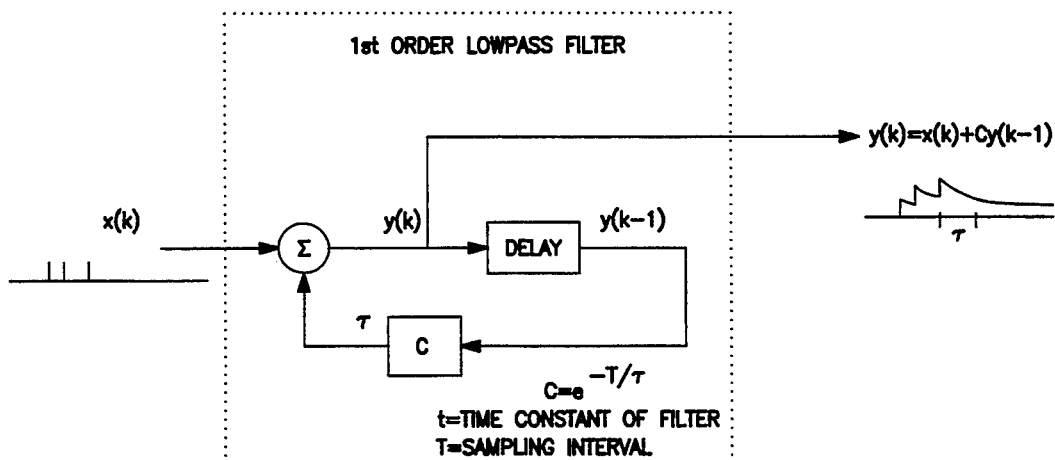
FIG. 9A illustrates a representative first order low pass filter.

FIG. 9A is a representative event counting filter.

Figure 9B:
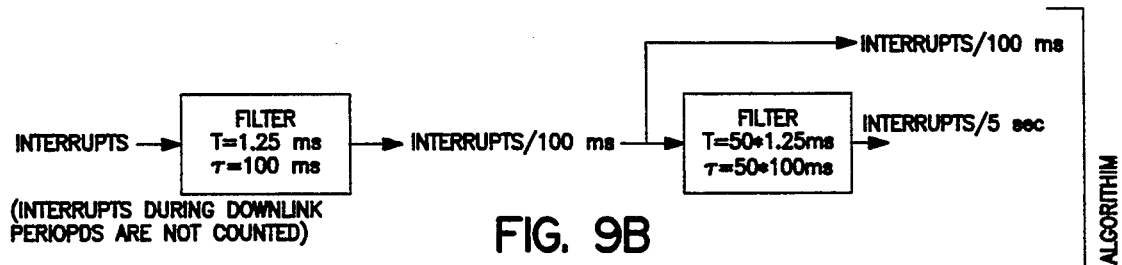
FIGS. 9B, 9C and 9D illustrate filters for the interrupts, artifacts, and pacemaker signals; and, FIG. 10 illustrates an automatic detection level adjustment flow chart.
Figure 9C:
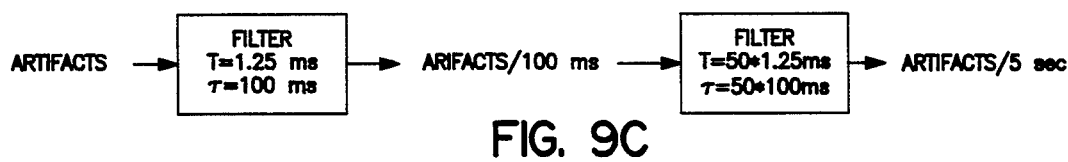
Figure 9D:

FIGS. 9B, 9C and 9D is the event counting filters which keep track of the a. time history of interrupts, b. artifacts that pass the screening criterion, and c. pacing markers available with many pacemaker systems. The filtered counts can be thought of as moving averages of the appropriate events over various time windows. Two time windows are used: 10 ms, and 5,000 ms (5 seconds).

Figure 10:
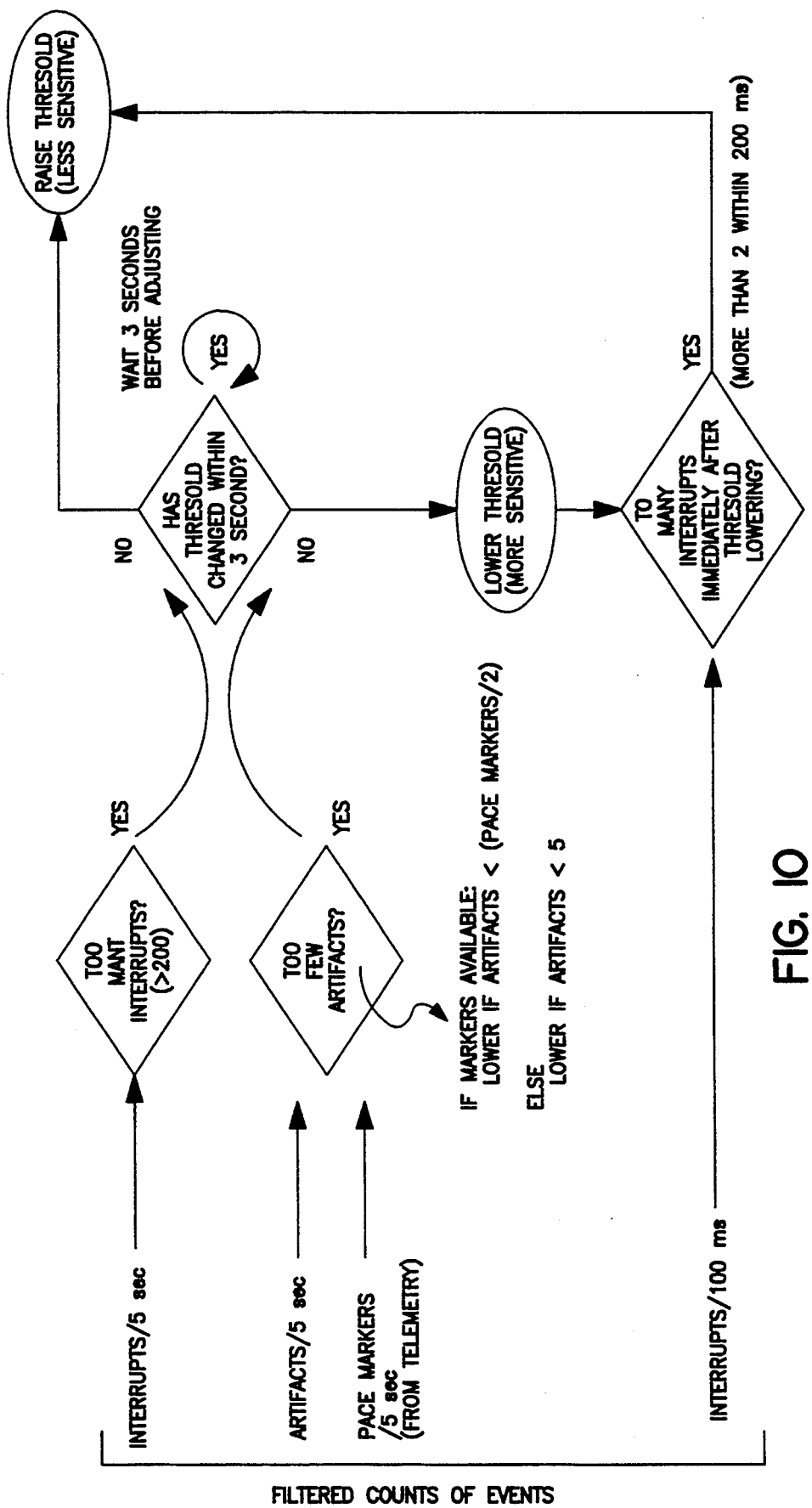

FIG. 10 is the automatic detection level adjustment algorithm which synthesizes the time history of the events from the event counting filters, and makes the decision to raise or lower the detection level or threshold. 5 seconds of data is used so that the threshold does not change prematurely due to momentary noise. Since the lowest allowed pacing rate is 1 pace every 2 seconds, at least 2-4 seconds must pass to determine that there has been no pacing in that time frame. When the threshold does change, 3 seconds must elapse before it is allowed to change again. This is to allow the new filtered counts to accurately reflect events due to the new threshold. One exception to the 3 second limit, however, is a quick test that is performed with every threshold lowering. During the 200 ms after the threshold is lowered, no artifacts are displayed, and any more than 2 interrupts will cause the threshold to immediately return to the next higher level. The assumption is that the interrupts were due to excessive noise at the lower level. This prevents the level from dropping below the noise floor in the absence of any pacing activity, causing false artifacts.

Various modifications of the present invention include the detection of pacing pulses in ECG signals, the detection and characterization of noise sources coupling into the ECG signal (pulse generator RF telemetry, for example). The values of times and frequencies are by way of example and for purposes of illustration of the present invention, and are not to be construed as limiting of the teachings and principals of the present invention.

The detection and characterization of other high frequency components of ECG signals (myopotentials, bad lead connections, sensor stimuli, for example). The detection and characterization of stimuli from other therapeutic devices coupling into the ECG signal (nerve stimulators, for example). The detection of pacing pulses in other cardiac signals, such as intracardiac electrograms. The output of the system can also be used as a trigger to control further analysis of the pacing pulse or ECG by: highlighting the pacing pulse to aid ECG analysis, removing the pacing pulse to aid ECG analysis, measuring amplitude and/or width of pacing pulses, characterizing pulse shape, storing/displaying the pacing pulse at high resolution, controlling an automatic capture detection system, and controlling an ECG analysis algorithm Amplitude data of pulses gathered from different lead configurations can also be used to do pacemaker lead position analysis or vector mapping.

We claim:

1. A heart pacing pulse detection system comprising:
   (a) means for inputing ECG signals;
   (b) a digital signal processor;
   (c) a multiplexer including a plurality of cardiac pacing artifact channel lines coupled to said inputting means and including select lines coupled to said digital signal processor;
   (d) a signal amplifier connected to said multiplexer and including a gain select line coupled to said digital signal processor;
   (e) a differentiator coupled to said signal amplifier;
   (f) a filter connected to said differentiator;
   (g) a bipolar comparator and signal squarer connected to said filter;
   (h) a programmable positive voltage reference and a programmable negative voltage reference connected between said bipolar comparator and said signal squarer and said select lines from said digital signal processor; (i) an optical isolator connected to said bipolar comparator and said signal squarer; (j) an inverter connected to said optical isolator and outputting an interrupt pulse to said digital signal processor; and (k) a state machine including a reset line from said digital signal processor and interval timer connected to said optical isolator and outputting data representative of a cardiac pacing pulse width to said digital signal processor.

2. The system of claim 1 wherein said multiplexer is 8 channels.

3. The system of claim 1 wherein said differentiator is about 30 kHZ.

4. The system of claim 3 wherein said differentiator is a high pass filter.

5. The system of claim 1 wherein said filter is a low pass filter.

6. The system of claim 5 wherein a pole of said low pass filter is about 100 kHZ.

7. The system of claim 1 wherein said positive voltage reference and said negative voltage reference generate positive and negative reference voltages respectively and wherein said digital signal processor selects a value for said reference voltages.

8. The system of claim 1 wherein said optical isolator is a high voltage optical isolator.

9. The system of claim 1 wherein said low pass filter includes a gain of about 2.

10. The system of claim 1 wherein said bipolar comparator and signal squarer is a voltage comparator.

11. A heart pacing pulse detection system comprising:
   (a) a plurality of ECG leads;
   (b) an analog detector connected to said plurality of ECG leads; and
   (c) a signal processor connected to said analog detector, said signal processor comprising:

(i) a timer control/interrupt handler connected to said analog detector;

(ii) a signal screener having an output and connected to said timer control/interrupt handler;

(iii) an event counter filter connected to said timer control/interrupt handler and said output of said signal screener; and (iv) an automatic detection level adjustment circuit connected between said event counter filter and said analog detector.

12. The system of claim 11 further comprising means for selecting which of said plurality of ECG leads are coupled to said analog detector.

13. A process for heart pacing pulse detection comprising the steps of (a) monitoring a patient's skin surface potentials;

(b) passing signals representative of said skin surface potentials through a differentiator and a low pass filter to generate filtered output signals;

(c) comparing said filtered output signals with predetermined programmable reference signals to generate interrupt signals;

(d) counting and filtering said interrupt signals to generate filtered counts of events, wherein said events are possible pacing artifacts; and (e) adjusting a predetermined detection level with respect to said filtered counts of events and adjusting said programmable reference signals in response to said adjusted predetermined detection level to detect pacing artifacts.

14. The process of claim 13 wherein said step of counting and filtering said interrupt signals comprises counting said filtered counts of events over 100 ms and 5000 ms time windows.

* * * * *